United States Patent [19]
Oliver et al.

[11] Patent Number: 5,290,268
[45] Date of Patent: Mar. 1, 1994

[54] DIAPER AND POUCH CONSTRUCTION

[76] Inventors: Charlotte J. Oliver; Carl R. Oliver, Jr., both of 1051 4th Ave., Apt. 66, Chula Vista, Calif. 91911

[21] Appl. No.: 977,196

[22] Filed: Nov. 16, 1992

[51] Int. Cl.$^5$ .................. A61F 13/15; A61F 13/20
[52] U.S. Cl. ................... 604/359; 604/358; 604/360; 604/385.1
[58] Field of Search ............... 604/358–360, 604/385.1; 2/111, 247, 250

[56] References Cited

U.S. PATENT DOCUMENTS

| | | | |
|---|---|---|---|
| 2,940,449 | 6/1960 | Thomson | 604/359 |
| 3,731,689 | 5/1973 | Schaar | 604/370 |
| 4,623,339 | 11/1986 | Ciraldo et al. | 604/360 |
| 4,790,307 | 12/1988 | Haber et al. | |
| 5,071,414 | 12/1991 | Elliott | 604/385.1 |
| 5,172,430 | 12/1972 | Solis | 2/400 |

Primary Examiner—Randall L. Green
Assistant Examiner—A. Zuttarelli
Attorney, Agent, or Firm—Leon Gilden

[57] ABSTRACT

A diaper is formed having a flexible fluid impermeable pocket web mounted to an exterior surface of the diaper web and to a second end thereof spaced from the first end to receive the furled diaper web within the pocket subsequent to its use. A modification of the invention includes tubular pockets positioned within the pocket web receiving frangible capsules having deodorizing fluid therewithin for rupturing and dispersion into the diaper to minimize unpleasant odors emanating therefrom.

2 Claims, 4 Drawing Sheets

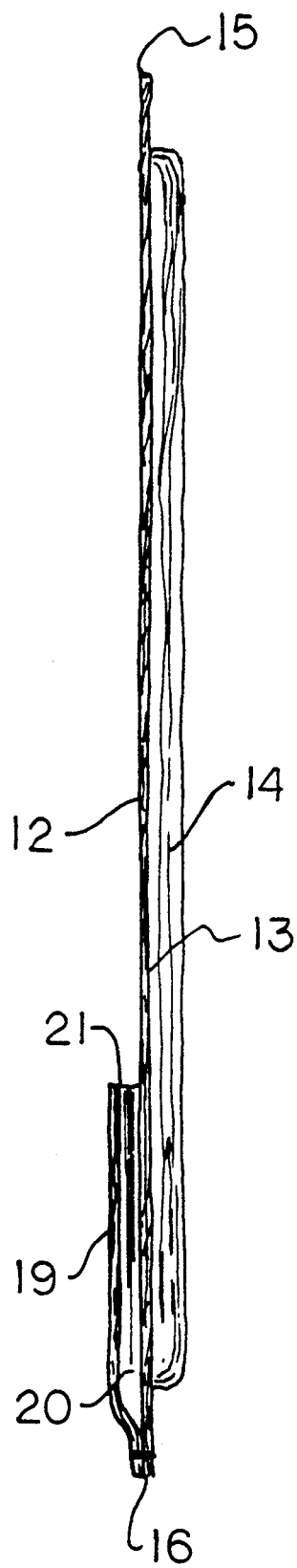
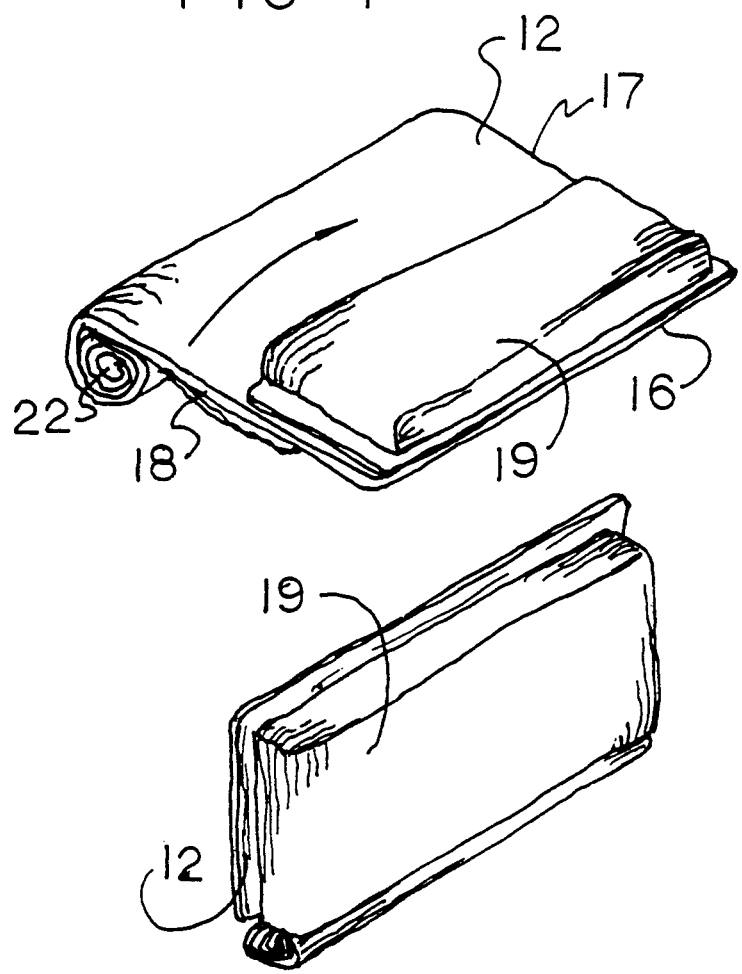
FIG 4
FIG 5
FIG 3

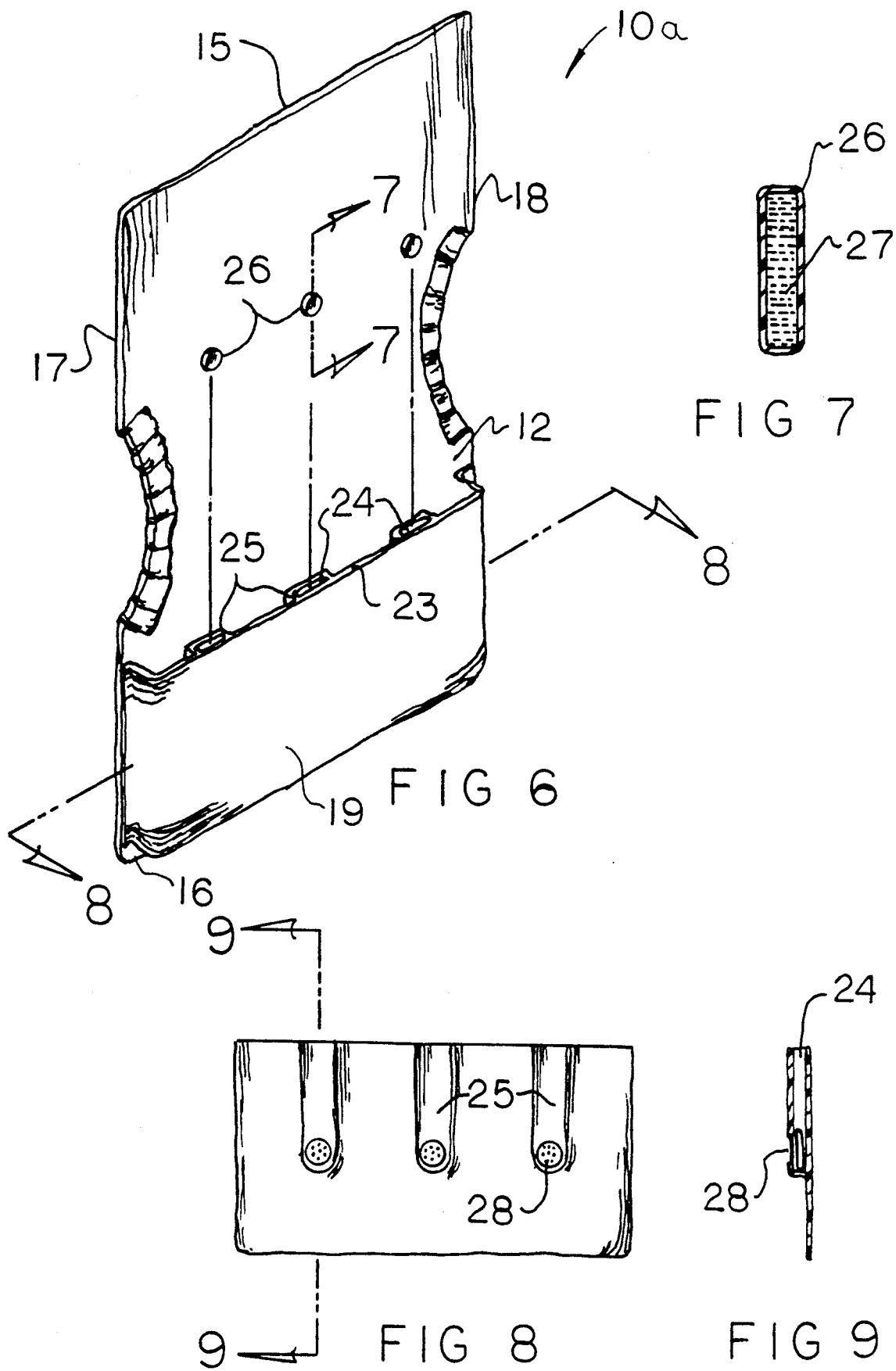

DIAPER AND POUCH CONSTRUCTION

BACKGROUND OF THE INVENTION

1. Field of the Invention

The field of invention relates to diaper construction, and more particularly pertains to a new and improved diaper and pouch construction wherein the same is arranged to provide for a pocket to receive the associated furled diaper subsequent to its use.

2. Description of the Prior Art

Diapers of various types have been utilized throughout the prior art and U.S. Pat. No. 4,938,755 to Foreman sets forth a diaper having a containment pocket having a closure means associated therewith directed within the diaper.

U.S. Pat. No. 4,964,859 to Feldman sets forth a diaper construction having an integral pad and disposal container associated therewith.

U.S. Pat. No. 5,037,414 to Booth sets forth a diaper having a liquid impervious back panel to receive a soiled diaper.

As such, it may be appreciated there continues to be a need for a new and improved diaper and pouch construction as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of diaper construction now present in the prior art, the present invention provides a diaper and pouch construction wherein the same is arranged to position a pocket to an exterior surface of a diaper to receive a furled component of the diaper within the pocket for disposal thereof. As such, the general purpose of the present invention, which will be described subsequently in greater detail, is to provide a new and improved diaper and pouch construction which has all the advantages of the prior art diaper and disposal pocket construction and none of the disadvantages.

To attain this, the present invention provides a diaper formed having a flexible fluid impermeable pocket web mounted to an exterior surface of the diaper web and to a second end thereof spaced from the first end to receive the furled diaper web within the pocket subsequent to its use. A modification of the invention includes tubular pockets positioned within the pocket web receiving frangible capsules having deodorizing fluid therewithin for rupturing and dispersion into the diaper to minimize unpleasant odors emanating therefrom.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved diaper and pouch construction which has all the advantages of the prior art diaper apparatus and none of the disadvantages.

It is another object of the present invention to provide a new and improved diaper and pouch construction which may be easily and efficiently manufactured and marketed.

It is a further object of the present invention to provide a new and improved diaper and pouch construction which is of a durable and reliable construction.

An even further object of the present invention is to provide a new and improved diaper and pouch construction which is susceptible of a low cost of manufacture with regard to both materials and labor, and which accordingly is then susceptible of low prices of sale to the consuming public, thereby making such diaper and pouch constructions economically available to the buying public.

Still yet another object of the present invention is to provide a new and improved diaper and pouch construction which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an orthographic view, taken along the lines 3—3 of FIG. 2 in the direction indicated by the arrows.

FIG. 4 is an isometric illustration of the diaper in a furled configuration preparatory to the positioning of the furled portion within the diaper pouch.

FIG. 5 is an isometric illustration of the furled diaper directed within the pouch.

FIG. 6 is an isometric illustration of a modified aspect of the diaper pouch construction.

FIG. 7 is an orthographic view, taken along the lines 7—7 of FIG. 6 in the direction indicated by the arrows.

FIG. 8 is an orthographic view, taken along the lines 8—8 of FIG. 6 in the direction indicated by the arrows.

FIG. 9 is an orthographic view, taken along the lines 9—9 of FIG. 8 in the direction indicated by the arrows.

DESCRIPTION OF THE PREFERRED EMBODIMENT

Figure 1:
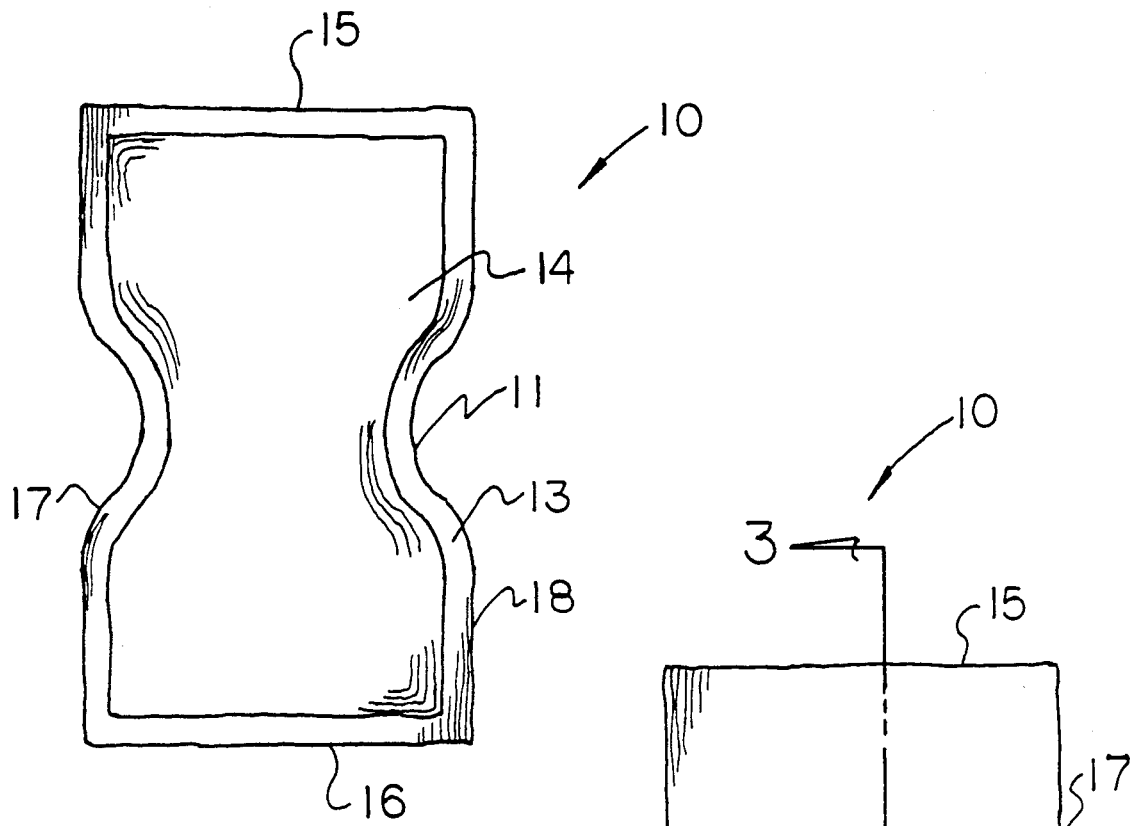
FIG. 1 is an orthographic view of the interior surface of the diaper.

With reference now to the drawings, and in particular to FIGS. 1 to 11 thereof, a new and improved diaper and pouch construction embodying the principles and concepts of the present invention and generally designated by the reference numeral 10 will be described.

More specifically, the diaper and pouch construction 10 of the instant invention essentially comprises a flexible diaper web 11 having an exterior first side 12 coextensive with an interior second side 13. A fibrous absorbent component 14 is mounted to the interior second side 13 within the diaper's webs first end 15, second end 16, first side 17, and second side 18. If desired, and as indicated per illustration, the first and second sides may utilize recesses for accommodating the infant's legs along the first and second sides when secured to the infant.

Figure 2:
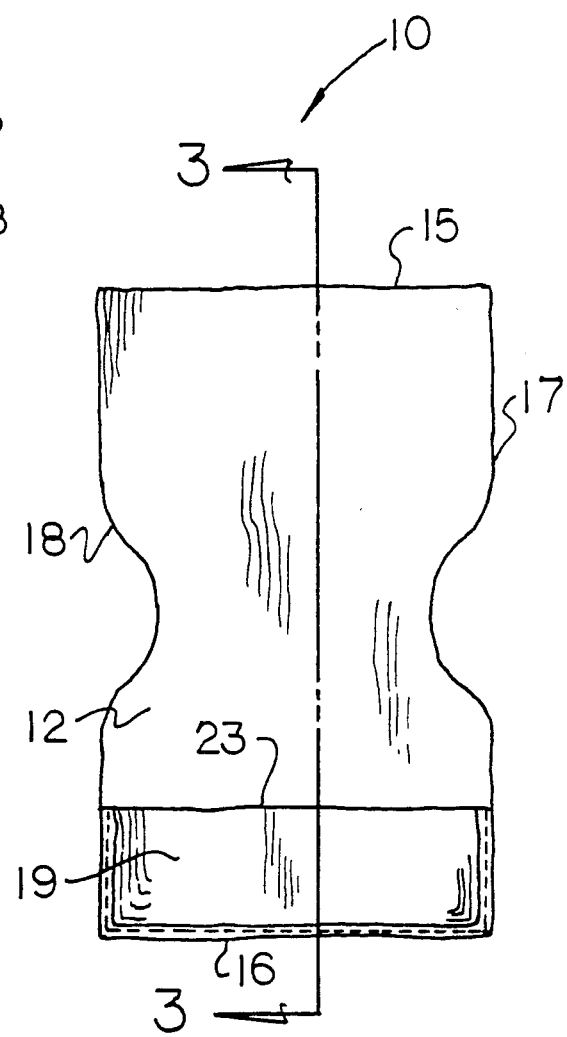
FIG. 2 is an orthographic view of the exterior surface of the diaper.

A pocket web 19 formed of a fluid impermeable material is mounted to the exterior first side 12 and having a continuous seam alone the first side 17, along the second end 16, and along a portion of the second side 18, with the pocket web 19 having a free edge 23 spaced below the first and second side recesses, as indicated in FIG. 2. The pocket web 19 accordingly defines a pocket cavity 20 between the pocket web 19 and the exterior first side 12, as illustrated in FIG. 3. The pocket cavity 20 accordingly is provided with an entrance opening 21 between the pocket web's free edge 23 and the first side 12. Accordingly in use, the diaper is furled to define a furled diaper 22, as indicated in FIG. 4, and subsequently the furled diaper directed into the pocket cavity 20 through the entrance opening 21, in a manner as indicated in FIG. 5.

The diaper and pouch construction 10a, as indicated in the FIG. 6 for example, is arranged to include elastomeric material coextensive with the side edges at the recesses to enhance securement relative to an infant's legs when secured to an infant. In particular, a plurality of tubular pockets 24 are mounted to the pocket web 19 between the pocket web 19 and the first side 12, with the tubular pockets 24 extending to the pocket web free edge 23. Within each pocket web, a frangible capsule 26 is directed having a deodorizing fluid 27 therewithin. In use, the frangible capsules 26 are crushed when the furled diaper 22 is directed into the pocket, and wherein the deodorizing fluid 27 is directed through the porous pocket web 25, as well as through a pocket web perforated window 28 directed through each pocket web 25 at a lower distal end of each tubular pocket 24, as indicated in FIG. 8 and FIG. 9.

Figure 10:
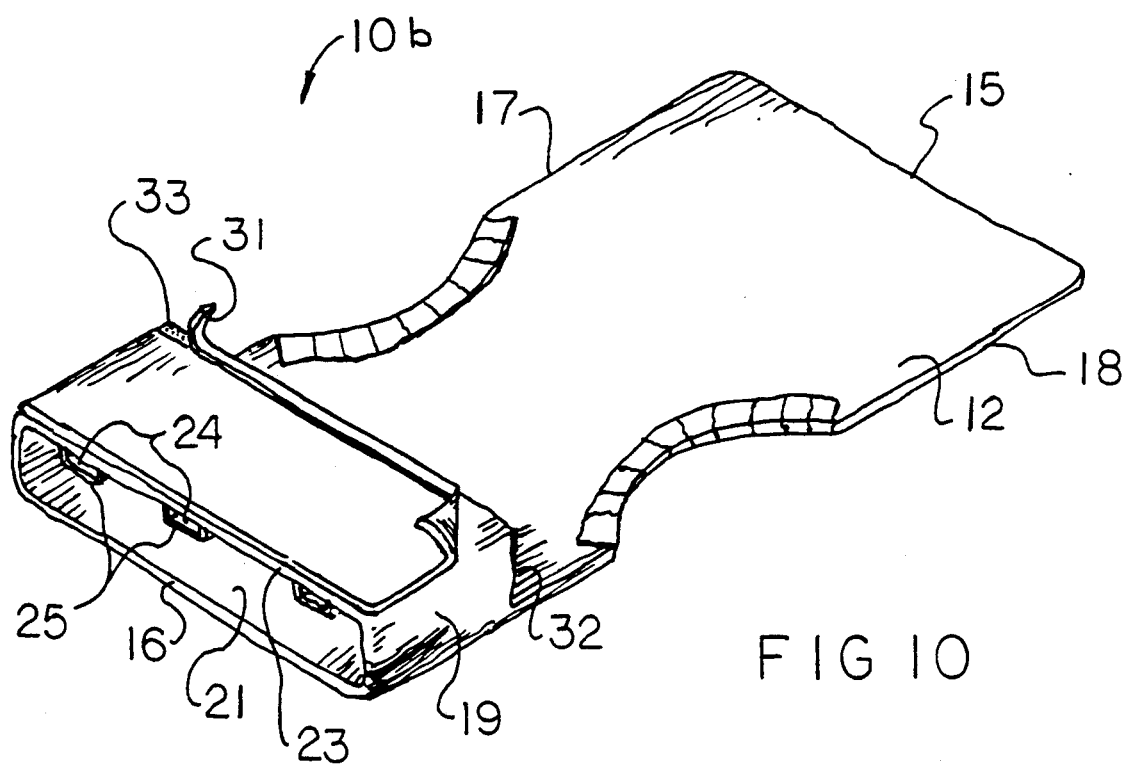
FIG. 10 is an isometric illustration of a modified diaper construction positioning the entrance of the pouch at the end portion of the diaper for receiving the furled diaper therewithin.
Figure 11:
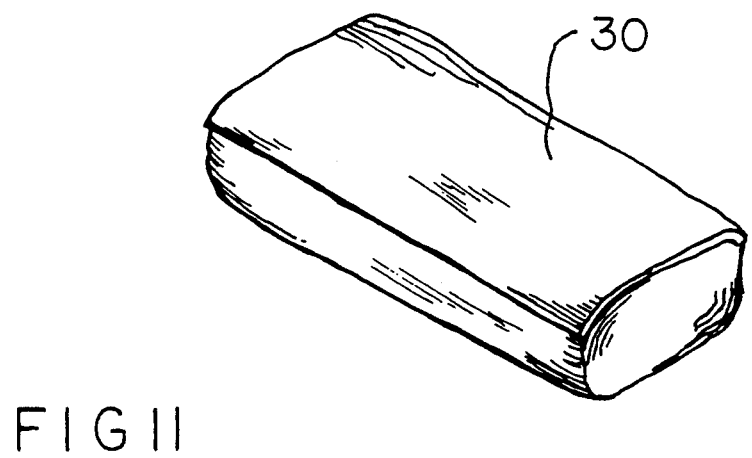
FIG. 11 is an isometric illustration of the diaper in a furled configuration in package form for disposal thereof.

The diaper construction 10b, as indicated in FIG. 10, positions the pocket cavity entrance opening 21 at the web second end 16 to receive the furled diaper component therewithin, as well as utilizing the tubular pocket construction 24 as well as the frangible capsule construction, in a manner as described in the FIGS. 6-9. The pocket web 19 includes a covering flap 30 hingedly mounted to the pocket web's free edge 23, wherein the cover flap 30 is separated relative to the pocket web 19 at the pocket floor 32 that is spaced from the entrance opening 21. An adhesive web 33 having a peel-away layer is mounted to the covering flap 30, whereupon removal of the peel-away layer, the adhesive web 33 is exposed to permit securement of the covering flap 30 onto the furled diaper component when directed within the pocket cavity 20.

In this manner, the diaper may be secured in a unitary package and the covering flap securable over the entrance opening as well as to the furled diaper component 22 to provide for the soiled diaper to be disposed in a convenient and compact manner.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A diaper and pouch construction, comprising,
 a flexible diaper web, the diaper web having an exterior first side coextensive with an interior second side, and a fibrous absorbing component mounted to the interior second side, with the web having a first end spaced from a second end, and a first side spaced from a second side, with the first side including a first side recess and the second side having a second side recess, and
 a pocket web having a pocket cavity formed of a fluid impermeable material directed and extending from the first side to the second side between the first side recess and the second side recess and the second end, with the pocket web having a pocket web free edge, and an entrance opening directed between the free edge and the exterior first side for access to said pocket cavity, and
 the free edge is positioned adjacent to the second end, and a plurality of tubular pockets mounted fixedly to the pocket web, wherein the tubular pockets extend from the free edge in a parallel relationship to each other, and each tubular pocket includes a pocket floor, and each tubular pocket including a porous pocket web, and each porous pocket web having a perforated window adjacent the pocket floor, and each tubular pocket further including a frangible capsule, with each frangible capsule including a deodorizing fluid therewithin permitting crushing of each capsule directing each deodorizing fluid through a respective perforated window.

2. A diaper and pouch construction as set forth in claim 1 including a covering flap, the covering flap hingedly mounted to the free edge, the covering flap having an adhesive web mounted to the covering flap spaced from the free edge, with the adhesive web having a removable strip thereover permitting removal of the removable strip for exposure of the adhesive web permitting securement of the adhesive web to the diaper web when the diaper web is in a furled configuration.

* * * * *